(12) United States Patent
Weber et al.

(10) Patent No.: US 9,687,154 B2
(45) Date of Patent: Jun. 27, 2017

(54) METHOD AND APPARATUS FOR 3D MEASUREMENT OF THE SKIN SURFACE AND NEAR-SURFACE SKIN LAYERS

(71) Applicant: MIKROSKIN GMBH, Oberhausen (DE)

(72) Inventors: Mark Weber, Moers (DE); Juergen Valentin, Duisburg (DE); Marcus Grigat, Wesel (DE)

(73) Assignee: MIKROSKIN GMBH, Oberhausen (DE)

( * ) Notice: Subject to any disclaimer, the term of this patent is extended or adjusted under 35 U.S.C. 154(b) by 0 days.

(21) Appl. No.: 14/890,681

(22) PCT Filed: May 12, 2014

(86) PCT No.: PCT/EP2014/001274
§ 371 (c)(1),
(2) Date: Nov. 12, 2015

(87) PCT Pub. No.: WO2014/183860
PCT Pub. Date: Nov. 20, 2014

(65) Prior Publication Data
US 2016/0081553 A1 Mar. 24, 2016

(30) Foreign Application Priority Data
May 15, 2013 (DE) .................. 10 2013 008 278

(51) Int. Cl.
*A61B 5/00* (2006.01)
*A61B 5/107* (2006.01)
(Continued)

(52) U.S. Cl.
CPC .......... *A61B 5/0068* (2013.01); *A61B 5/1079* (2013.01); *A61B 5/441* (2013.01);
(Continued)

(58) Field of Classification Search
CPC ... G06T 7/50; G06T 7/55; G06T 2207/30088; G02B 21/0028; G02B 21/004;
(Continued)

(56) References Cited

U.S. PATENT DOCUMENTS

| | | | |
|---|---|---|---|
| 2007/0263226 A1 | 11/2007 | Kurtz et al. | 356/492 |
| 2010/0214562 A1 | 8/2010 | Mahadevan-Jansen et al. | 356/301 |
| 2014/0049632 A1* | 2/2014 | Hemmer | 348/79 |

FOREIGN PATENT DOCUMENTS

EP 1 607 041 A2 12/2005 ............. A61B 5/107

OTHER PUBLICATIONS

Confocal Laser Scanning Microscopy—In Vivo Histology for Cellular Level Skin Analyses in Cosmetic Research and Dermopharmacy, VivaScope , Pigmentation and Whitening Aging Inflammatory Cutaneous Status Aesthetic Dermatology Wound Healing and Scars Penetration Antiperspirants, Apr. 1, 2011, pp. 1-20.

(Continued)

*Primary Examiner* — Andrew W Johns
(74) *Attorney, Agent, or Firm* — Collard & Roe, P.C.

(57) ABSTRACT

The invention relates to a method for the 3D measurement of the skin surface and near-surface skin layers by means of a confocal sensor with integrated color camera arranged in a handheld device, wherein said handheld device being moved by an operator via a sensor head to the location of the skin to be examined and a color image of the skin surface then being captured, whereupon the sensor being automatically changed over to confocal operation during which an image stack is generated by the simultaneous capturing of a multitude of all pixels necessary to create a complete image, said stack consisting of confocal images extending into the interior of the skin, with the entire area extending axially into the skin interior being scanned layer by layer in Z (Continued)

direction, wherein after capturing the measuring data an evaluation is performed resulting in a 3D image of the topography of the skin to be generated, and, moreover, from the image stack captured sectional images of the skin and skin volume are computed down to a depth of several millimeters and the images so created being displayed on a monitor.

8 Claims, 2 Drawing Sheets

(51) Int. Cl.
    *G01B 11/24*     (2006.01)
    *G02B 21/00*     (2006.01)
    *G06T 3/40*     (2006.01)
    *G06T 5/50*     (2006.01)

(52) U.S. Cl.
    CPC ............ *G01B 11/24* (2013.01); *G02B 21/004* (2013.01); *G02B 21/006* (2013.01); *G02B 21/0028* (2013.01); *G06T 3/4038* (2013.01); *G06T 5/50* (2013.01); *A61B 5/0035* (2013.01); *A61B 2576/02* (2013.01); *G06T 2207/30088* (2013.01)

(58) Field of Classification Search
    CPC ... G02B 21/006; A61B 5/0035; A61B 5/0037; A61B 5/0064; A61B 5/0068; A61B 5/441; A61B 2576/02
    See application file for complete search history.

(56) References Cited

OTHER PUBLICATIONS

Christopher L. Arrasmith et al: "MEMS-based handheld confocal microscope for in-vivo skin imaging," Optics Express, vol. 18, No. 4, Feb. 11, 2010, pp. 3805-3819.
Loewke, Kevin et al: "Real-time image mosaicing with a hand-held dual-axes confocal microscope", SPIE, vol. 6851, Feb. 5, 2008, pp. 68510F-1-68510F-9.
International Search Report of PCT/EP2014/001274, mailed Aug. 27, 2014.

* cited by examiner

METHOD AND APPARATUS FOR 3D MEASUREMENT OF THE SKIN SURFACE AND NEAR-SURFACE SKIN LAYERS

CROSS REFERENCE TO RELATED APPLICATIONS

This Application is the National Stage of PCT/EP2014/001274 filed on May 12, 2014, which claims priority under 35 U.S.C. §119 of German Application No. 10 2013 008 278.1 filed on May 15, 2013, the disclosure of which is incorporated by reference. The international application under PCT article 21(2) was not published in English.

The invention relates to a method aimed at taking 3D measurements or surveys of the skin surface and near-surface skin layers by means of a confocal sensor with integrated color camera arranged in a handheld device.

As is commonly known, the confocal technology is employed with view to measuring the topography of the surfaces of materials for industrial applications. In the biological field, confocal microscopy is also known, i.e. to prepare sectional images of certain surfaces, said technique is usually adopted because of its high degree of depth discrimination more often than not with fluorescence markers. Moreover, it is also known that infrared light is capable of illuminating/revealing the skin structure so that said structure can be examined microscopically.

Publication US 2010/0214562 A1 describes an apparatus by means of which the skin surface or near-surface skin layers is/are scanned consecutively on a pixel by pixel basis resulting in an image being created that is composed of these pixels.

A similar device has been disclosed in US 2007/0263 226 A1. In that case, pinhole-like modulator arrays are used making it possible in each measurement to scan, for example, five pixels on the skin simultaneously. Following this, the array is displaced laterally in order to scan five additional pixels.

Both devices and the methods implemented with them thus suffer from the disadvantage that a fast measurement cannot be accomplished due to the necessary lateral scan on the one hand and the poor light yield on the other. As such, the handling characteristics of both known devices are unsatisfactory because blur due to camera shaking must be expected as a result of the slowness of measurement and poor light yield.

Moreover, tomographic methods as well as puncturing techniques are known to enable examinations of deeper skin areas to be performed. Tomographic procedures are sophisticated and costly. A puncturing method, for example with a view to detecting skin cancer, has the disadvantage that carcinomas have to be opened which is associated with the increased risk of the cancer spreading further.

Objective of the present invention is to provide and perform with a single device a method by means of which both the skin surface can be surveyed three-dimensionally in vivo and, also in vivo, the structure of the skin can be determined to a depth of several millimeters, with the capturing speed and the light yield being significantly higher and movable elements avoided to the greatest extent possible in comparison to what is offered by the state of the art.

Said objective is accomplished by providing a method for the 3D measurement of the skin surface and near-surface skin layers by means of a confocal sensor with integrated color camera arranged in a handheld device, with said handheld device being moved by an operator via a sensor head to the location of the skin to be examined and a color image of the skin surface then being captured, whereupon the sensor being automatically changed over to confocal operation during which an image stack is generated by the simultaneous capturing of a multitude of all pixels necessary to create a complete image, said stack consisting of confocal images extending into the interior of the skin, with the entire area extending axially into the skin interior being scanned layer by layer in Z direction, whereupon after capturing the measuring data an evaluation is performed resulting in a 3D image of the topography of the skin to be generated, and, moreover, from the image stack captured sectional images of the skin and skin volume are computed down to a depth of several millimeters and the images so created being displayed on a monitor.

Moreover, the objective is also reached by providing a device for the implementation of the method, said device consisting of a confocal sensor with a stationarily disposed microlens array arranged in a portable enclosure, said confocal sensor having a monochromatic radiation source, and the device further comprising an overview color camera with white light illumination source, wherein the camera can be enabled to access the measuring path by means of a beam splitter, and both the camera and the confocal sensor being connected with a signal evaluation unit. Said evaluation unit can be linked to an external monitor.

The measuring head is thus a handheld component which when placed onto the skin surface is capable of carrying out a complete survey within a few seconds, such a survey comprising:
Capturing a color image,
Measuring the 3D structure of the skin surface,
Capturing a 3D image (contrast image) of the inner structure of the skin.

With the help of the overview color camera integrated into the sensor and a monitor connected the relevant skin location is initially searched for making use of a scan field of view several millimeters in size. This is facilitated by the very compact dimension of the sensor head the size of which only slightly exceeds that of the scan field of view. In this way and by visual observation the sensor head is first moved to the desired location, with the area to be examined then approached with the aid of the life color image on the monitor. Since the image is sharp up to a few millimeters (approx. 5 mm) away from the sensor head the device can be placed onto or moved over the skin a short distance away from it.

When the desired area has been found the sensor is switched over to confocal operation within only a few milliseconds causing an image stack to be captured in a few seconds that consists of hundreds of confocal images (typically are 200 to 1000 images). By simultaneously capturing the number of pixels required for the image an image is created in real time for the respective stack through the use of a stationarily arranged microlens array. While the image is being captured a scanner arranged in the sensor makes sure the entire axial measuring range (Z direction) is passed through. The captured image stack consists of equidistant individual images.

Moreover, being part of the optical system itself the use a microlens array offers the added advantage that it also contributes to the compactness of the device.

After the measuring data have been acquired their evaluation takes place as follows:
1. The position of the topmost reflection (nearest to the sensor head) is asesssed which yields information about the 3D topography.

2. Same as in computer tomography sectional images of and through the skin structure are created. These can be analyzed with respect to structure and contrast.
3. The previously taken color image is displayed as overlay of the 3D topography. In this way, conspicuous pigmentation can be overlaid microscopically through the existing 3D topography.

By repeated capturing the scan field of view can be expanded automatically. After the stack image has been taken an acoustic signal, for example, is given informing the operator that a new laterally displaced stack image can be initiated. Thus, the scan field of view is enlarged through repeated image capturing. The different images can then be assembled—similar to stitching—to create an overall image.

In a further feature is provided that after and in addition to the evaluation described hereinbefore a high-speed real-time image can be generated by shifting the focus onto an interesting depth section, for example with a view to measuring the flow of blood in certain areas. Thus, for the generation of a sectional image in real time the focus is purposefully directed in a confocal manner to a certain skin depth and a continuous series (stream) of images is captured.

In a further feature according to the invention, the confocal sensor is provided with a matrix sensor of CMOS or CCD technology, likewise the overview color camera.

To enable the interior of the skin to be investigated the confocal sensor has a monochromatic radiation source, in this case an infrared radiation source with an emitting range of between 800 and 950 nm, where a measuring wavelength of 850 nm or 940 nm is also suitable.

The device proposed as per the present invention can be employed in cancer diagnosis for early recognition, for observation purposes, and to detect changes. Moreover, cosmetic effects can be monitored, for example the penetration depth of cosmetic preparations as well as the depth effect of a treatment. The skin thickness and structure may as well be determined in the case of burn injuries or skin transplantations, with the examination results being available within a few seconds thanks to the inventive technology and by using a single device only.

With reference to FIGS. 1 and 2 the invention is elucidated in detail hereinafter, where:

Figure 1:
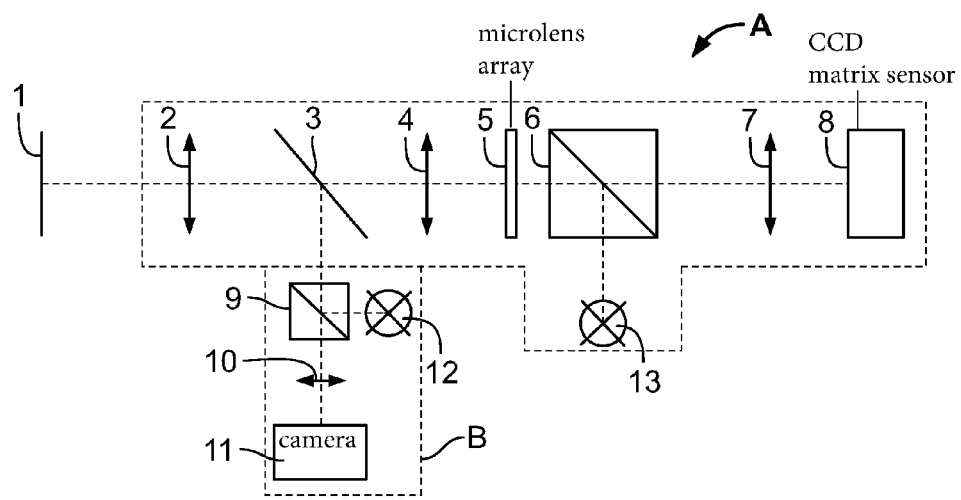
FIG. 1 is the schematic representation of the optical configuration of the inventive device.

In FIG. 1 the configuration of the optical system of the inventive device is shown schematically. It mainly consists of groups A and B, with group A depicting the confocal measuring arrangement while group B shows a digital color camera.

The object plane (which in this case is the skin surface) has been identified by reference numeral 1. Inside the device, reference numeral 2 identifies a focusing lens that serves to focalize the monochromatic (infrared) light emitted by the collimated radiation source 13 as well as the light stemming from the also collimated white light source 12 onto the object plane 1. Via an additional focusing lens 4 and microlens array 5 arranged in the intermediate image plane the light reflected by the object plane is projected onto a CCD matrix sensor 8 by imaging optics 7 consisting of the elements 21, 22, 23 shown in FIG. 2, and, respectively, via the beam splitter 3 and the imaging optics 10 onto matrix sensor 11 (camera).

The lens 4 is the only movable element of the arrangement because it serves to perform the focusing needed for capturing the layered image.

Figure 2:
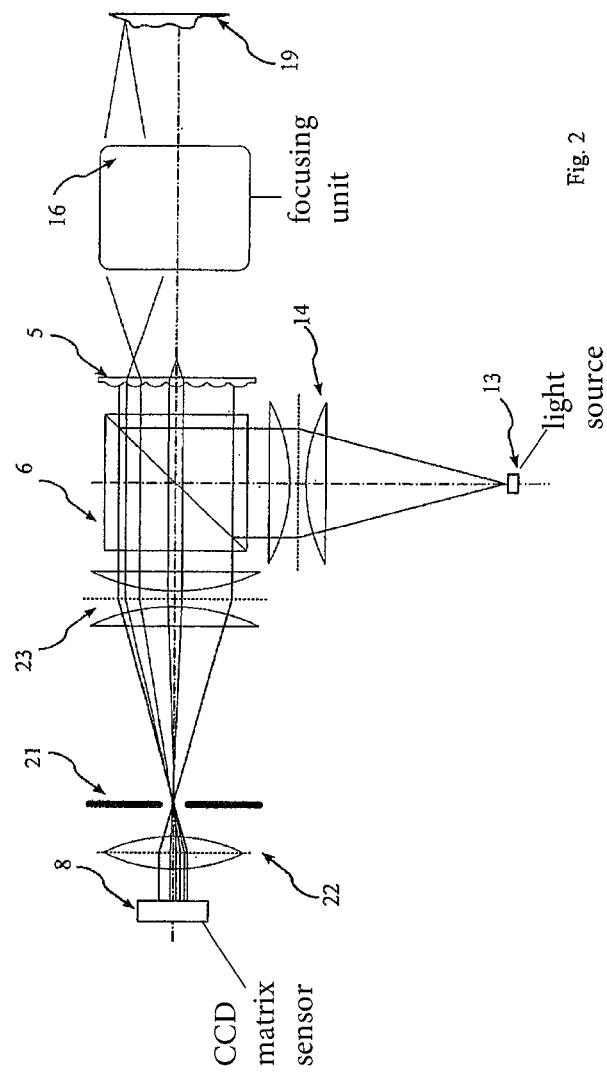
FIG. 2 is a detailed representation of the design of the confocal sensor.

As is evident from FIG. 2, the microlens array 5 is of rectangular or square shape and said array is arranged so as to be stationarily located in the beam path and enables a complete layered image to be captured simultaneously in real time. Microlens arrays of this type feature very small gaps between lenses (e.g. 30 μm), with the lenses typically having a circular shape and being arranged in square or hexagonal packings. In the arrangement shown in FIG. 2 which is a central component of the confocal measuring system the light emitted by light source 13 is projected as parallel light from a collector lens 14 via a beam splitter 6 onto the microlens array 5. The microlenses 5 generate many reduced-in-size images of the light source. The focusing unit 16 (reference numerals 2 and 4 in FIG. 1) directs the foci of the microlenses onto the object 19. Via the above described elements 16, 5, and 6 the light reflected from object 19 is focused with the aid of focusing optics 23 onto the aperture opening 21 and via lens 22 directed towards the CCD sensor.

The opening diameter of aperture 21 has been provided so as to correspond to the emission surface of light source 13.

In group B, the focusing optics 10 is shown to be located between the color camera 11 and a beam splitter 9. By action of beam splitter 9 the light emitted by the white-light radiation source 12 is guided into the optical path of the confocal sensor A where it is projected by means of semi-transparent mirror 3 (beam splitter) onto the object plane 1 of object 19.

Figure 3:
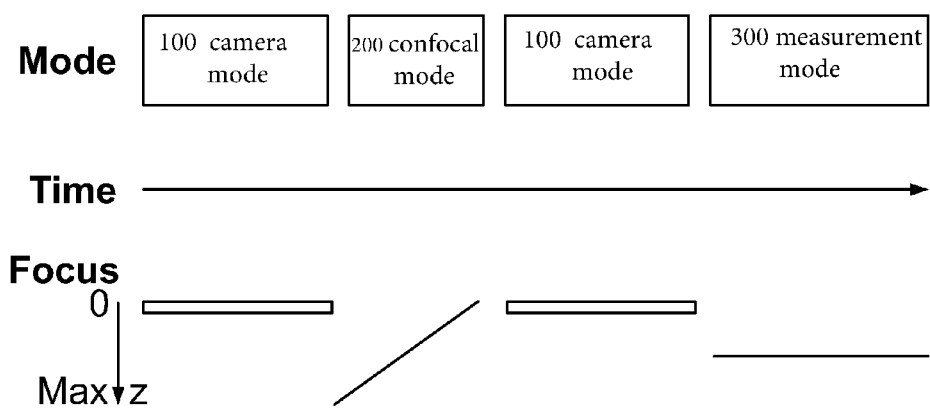
FIG. 3 shows a flowchart of the measurement.

In FIG. 3 the time flow of a measurement is shown, with mode 100 in this case indicating that a life color camera stream of measured object 19 is captured by means of a color camera (group B) and that the image taking duration is operator controlled (overview image).

In mode 200 the camera mode is changed over to the confocal mode. A fast confocal measurement including depth scan takes place (which is signified by the inclined representation). In this case, the focus plane 1 is shifted through the entire volume of measured object 19.

During the measurement, an overview image of the skin surface is created initially followed by the confocal measurement through which information is obtained about the 3D topography of the skin surface down to a depth of several millimeters.

Using an infrared light source for the confocal measurement enables the interior of the skin to be surveyed, with, as described hereinbefore, a stack of images being generated in each case by axial scanning. By means of the evaluation unit (not shown here) the measured data are transformed into layered images of the skin (also in terms of volume) and displayed on an (external) monitor which has not been represented here either.

Subsequently (in mode 100), another life color image can be produced whereas mode 300 in the end enables the focus to be directed in a confocal manner to a certain depth with a stream of images then being captured.

Taking measurements in mode 300 makes it possible, for example, to represent in real time and/or evaluate the flow of blood at certain depth levels.

The invention claimed is:
1. Method for the 3D measurement of the skin surface and near-surface skin layers by means of a confocal sensor with integrated color camera arranged in a handheld device, wherein said handheld device being moved by an operator via a sensor head to the location of the skin to be examined and a color image of the skin surface then being captured, whereupon the sensor being automatically changed over to confocal operation during which an image stack is generated by the simultaneous capturing of a multitude of all pixels necessary to create a complete image, said stack comprising confocal images extending into the interior of the skin, with the entire area extending axially into the skin interior being scanned layer by layer in Z direction, wherein after capturing the measuring data an evaluation is performed resulting in a 3D image of the topography of the skin to be generated, and, moreover, from the image stack captured sectional images of the skin and skin volume are computed down to a depth of several millimeters and the images so created being displayed on a monitor.

2. The method according to claim 1, wherein the scan field of view is enlarged through repeated image capturing and the individual image stacks are combined to form an overall image (stitching).

3. The method according to claim 2, wherein after the image stack has been completed a signal is given informing the operator that the next image stack can be captured.

4. The method according to claim 1, wherein for the generation of a sectional image in real time the focus is purposefully directed in a confocal manner to a certain skin depth and a continuous series (stream) of images is captured.

5. The method according to claim 1, wherein said confocal sensor comprises a portable enclosure and a stationarily disposed microlens array arranged in the portable enclosure, said confocal sensor having a monochromatic radiation source,
   wherein said integrated color camera is an overview color camera and comprises a white light illumination source,
   wherein the camera accesses a measuring path via a beam splitter, and
   wherein both the overview color camera and the confocal sensor are connected with a signal evaluation unit, the signal evaluation unit performing the evaluation.

6. The method according to claim 5, wherein the confocal sensor is provided with a CCD or CMOS matrix sensor, with the overview color camera also being provided with a matrix sensor.

7. The method according to claim 5, wherein the monochromatic radiation source of the confocal sensor is an infrared source with an emission range of between 800 and 950 nm.

8. The method according to claim 7, wherein the wavelength is 850 nm or 940 nm.

* * * * *